United States Patent
Li et al.

(10) Patent No.: US 8,309,491 B2
(45) Date of Patent: Nov. 13, 2012

(54) STABLE EMULSIFIABLE CONCENTRATES CONTAINING A FIRST HERBICIDAL CARBOXYLIC ACID SALT AND A SECOND HERBICIDAL CARBOXYLIC ACID ESTER

(75) Inventors: Mei Li, Westfield, IN (US); Holger Tank, Zionsville, IN (US); Melissa G. Olds, Zionsville, IN (US); Derek J. Hopkins, New Plymouth (NZ); Robert M. Buttimor, New Plymouth (NZ)

(73) Assignee: Dow AgroSciences, LLC, Indianapolis, IN (US)

( * ) Notice: Subject to any disclaimer, the term of this patent is extended or adjusted under 35 U.S.C. 154(b) by 196 days.

(21) Appl. No.: 12/607,709

(22) Filed: Oct. 28, 2009

(65) Prior Publication Data

US 2010/0105558 A1 Apr. 29, 2010

Related U.S. Application Data

(60) Provisional application No. 61/109,196, filed on Oct. 29, 2008.

(51) Int. Cl.
*A01N 43/40* (2006.01)
*A01N 47/10* (2006.01)
*A01N 37/00* (2006.01)
*A01N 25/00* (2006.01)

(52) U.S. Cl. ......... 504/130; 504/135; 504/142; 504/363
(58) Field of Classification Search .................. 504/363, 504/130, 142, 135
See application file for complete search history.

(56) References Cited

U.S. PATENT DOCUMENTS

| 5,466,659 A | 11/1995 | Keeney et al. |
| 5,965,487 A * | 10/1999 | Flahive .......................... 504/130 |
| 2007/0117721 A1 | 5/2007 | Keeney et al. |

FOREIGN PATENT DOCUMENTS

| WO | WO 9424866 A1 * | 11/1994 |
| WO | WO9628027 | 9/1996 |
| WO | WO 2004093546 | 11/2004 |
| WO | WO 2007/094836 A1 | 8/2007 |
| WO | WO 2010/053784 | 5/2010 |
| WO | WO 2010053784 | 5/2010 |

OTHER PUBLICATIONS

Garlon 3A Herbicide, Material Safety Data Sheet, 2006, Dow AgroSciences, pp. 1-5.*
Mann R K et al: "Biology and Control of Tall Ironweed (Veronia Altissima)", Weed Science, Weed Sciences Society of America, Champaign, IL, US, vol. 31, No. 3, May 1, 1983, pp. 324-328, XP-0144997, ISSN: 0043-1745.
Anderson T M D et al: "Fireweed response to boomspray applications of different herbicides and adjuvants", Plant Protection Quarterly, Inkata Press, North Clayton, AU, vol. 10, No. 4, Jan. 1, 1995, pp. 152-153, XP009144994, ISSN: 0815-2195.

* cited by examiner

*Primary Examiner* — John Pak
*Assistant Examiner* — Andriae M Holt
(74) *Attorney, Agent, or Firm* — Robert Chang

(57) ABSTRACT

Stable emulsifiable concentrates containing a first herbicidal carboxylic acid in the salt form and a second herbicidal carboxylic acid in the ester form are prepared by using a tertiary amine to prepare the salt of the first herbicidal carboxylic acid and by using an alcohol which is the same as the ester portion of the second carboxylic acid herbicide as the solvent.

5 Claims, No Drawings

US 8,309,491 B2

STABLE EMULSIFIABLE CONCENTRATES CONTAINING A FIRST HERBICIDAL CARBOXYLIC ACID SALT AND A SECOND HERBICIDAL CARBOXYLIC ACID ESTER

FIELD OF THE INVENTION

This application claims the benefit of U.S. Provisional Application Ser. No. 61/109,196 filed on Oct. 29, 2008. This invention concerns a novel stable emulsifiable concentrate containing a first herbicidal carboxylic acid in the salt form and a second herbicidal carboxylic acid in the ester form.

BACKGROUND OF THE INVENTION

To design an agricultural formulation product, the most important question to be answered is its stability. Failure to meet a set of stability requirements which usually depend on the specific market, application and regulations will certainly lead to failure of its commercialization. There are many causes of formulation instabilities, such as a) chemical instabilities due to reactions between ingredients (actives and/or inerts, etc.), photo-degradations, and oxidations, etc., b) physical instabilities due to phase separations (Oswald ripening, crystallization, sedimentations, creamings, etc.) and c) environmental factors (temperature, humidity/moisture, etc.). In today's agrochemical market, it becomes increasingly common to design formulations to contain multiple active ingredients and their required solvents, safeners, and/or adjuvants, etc., in order to achieve the optimal spectrum, efficacy, and delivery efficiency, which consequently makes formulation stability more and more challenging. Therefore, technologies that can effectively isolate, hinder, or eliminate, adverse reactions or interactions between incompatible ingredients are often critical for a successful product.

The emulsifiable concentrate, a liquid homogeneous formulation to be applied as an emulsion after dilution in water, is one of the most common formulation types for many agricultural products. Emulsifiable concentrates are mixtures of an oil-soluble active ingredient and emulsifying agents dissolved in an organic solvent. The emulsifying agent enables the emulsifiable concentrate to disperse easily in water, thereby forming a "milky" and homogenous emulsion. Emulsifiable concentrates require tank agitation to form the emulsion and maintain it during spraying. However, many challenges may exist, when, for instance, active ingredients may react with one another or with other ingredients in the formulation. For example, a composition containing triclopyr butoxyethyl ester and aminopyralid acid or its potassium salt has been found to be extremely useful for the control of brush and woody plants in range and pasture and industrial vegetation management applications. In some typical emulsifiable concentrate formulations with the hydrophobic ester herbicide and the hydrophilic acid or salt herbicide, only small amounts of the hydrophilic herbicide may dissolve in the organic solvent. In typical emulsifiable concentrate formulations with the hydrophobic ester herbicide and the hydrophilic acid herbicide dissolved in the oil phase, the acid herbicide may decarboxylate upon storage at elevated temperatures. In typical emulsifiable concentrate formulations with the hydrophobic ester herbicide and the hydrophilic salt herbicide dissolved in the oil phase, the hydrophilic salt herbicide may react with the oil-soluble ester herbicide, leading to hydrolysis or transesterification. It would be desirable to have a more stable emulsifiable concentrate containing a first herbicidal carboxylic acid in the salt form and a second herbicidal carboxylic acid in the ester form.

SUMMARY OF THE INVENTION

The present invention concerns a stable emulsifiable concentrate which comprises:
a) a first carboxylic acid herbicide in the form of a tertiary amine salt in which the tertiary amine has the formula

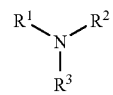

wherein $R^1$, $R^2$ and $R^3$ independently represent a $C_1$-$C_{18}$ alkyl, optionally substituted with hydroxyl, amino or alkoxy groups;
b) a second carboxylic acid herbicide in the form of a $C_4$-$C_8$ alkyl or alkoxy-substituted alkyl ester;
c) an alcohol solvent or co-solvent which is the same as the ester portion of the second carboxylic acid herbicide ester; and
d) optionally emulsifiers.

Another aspect of the present invention concerns a method of preparing the emulsifiable concentrate which comprises contacting the first carboxylic acid herbicide in the acid form with the tertiary amine in the alcohol solvent and with the second carboxylic acid herbicide ester and optionally any emulsifiers with stirring until a homogeneous solution is obtained.

DETAILED DESCRIPTION OF THE INVENTION

This invention provides a stable emulsifiable concentrate containing a first herbicidal carboxylic acid in the salt form and a second herbicidal carboxylic acid in the ester form. The first carboxylic acid herbicide is in the form of a tertiary amine salt in which the tertiary amine has the formula

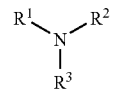

wherein $R^1$, $R^2$ and $R^3$ independently represent a $C_1$-$C_{18}$ alkyl, optionally substituted with hydroxyl, amino or alkoxy groups.

Preferably, at least one of $R^1$, $R^2$ and $R^3$ represents a $C_{12}$-$C_{18}$ alkyl group. The tertiary amines include, but are not necessarily limited to, a tertiary alkylamine, a tertiary alkanolamine, a tertiary ethoxylated alkylamine, a tertiary propoxylated alkylamine, a tertiary alkyldiamine, a tertiary ethoxylated alkyldiamine, a tertiary propoxylated alkyldiamine and mixtures thereof. The solvent or co-solvent is an alcohol which is the same as the ester portion of the second carboxylic acid herbicide ester.

The term "alkyl", as used herein, includes within its scope straight chain, branched chain and cyclic hydrocarbon groups, which may be saturated or unsaturated. Unsaturated hydrocarbon groups may contain more than one unsaturated bond.

The herbicidal carboxylic acids useful in the emulsifiable concentrates of the present invention are well known in the art and are described, for example, in *The Pesticide Manual*, Fourteenth Edition, 2006. Preferred examples of herbicidal carboxylic acids include phosphorus-containing carboxylic acids such as glufosinate and glyphosate; benzoic acid herbicides such as dicamba; phenoxyalkanoic acid herbicides such as 2,4-D, MCPA or 2,4-DB; aryloxyphenoxypropionic acid herbicides such as clodinafop, cyhalofop, fenoxaprop, fluazifop, haloxyfop and quizalofop; and pyridinecarboxylic acid and picolinic acid herbicides such as aminopyralid, clopyralid, fluoroxypyr, picloram and triclopyr.

Preferred examples of the first carboxylic acid herbicide in the form of an amine salt include the amine salts of aminopyralid, picloram, clopyralid, and triclopyr.

Preferred examples of the second carboxylic acid herbicide in the form of a $C_4$-$C_8$ alkyl or alkoxy-substituted alkyl ester include triclopyr butotyl (butoxyethyl ester), fluoroxypyr meptyl (1-methylheptyl ester), and picloram isooctyl (2-ethylhexyl ester).

The amine salts of a tertiary amine include but are not limited to a tertiary alkylamine, a tertiary alkanolamine, a tertiary ethoxylated alkylamine, a tertiary propoxylated alkylamine, a tertiary alkyldiamine, a tertiary ethoxylated alkyldiamine, a tertiary propoxylated alkyldiamine and mixtures thereof. The tertiary alkylamines as used herein refer to trialkyl amines in which at least one of the alkyl groups is a $C_{12}$-$C_{18}$ alkyl group. The Armeen™ products of Akzo Nobel, such as Armeen DMTD, Armeen DMCD, Armeen DMOD, Armeen DMSD, Armeen M2C, Armeen M2HT, Armeen 312, Armeen 316 and Armeen 380 are typical tertiary alkylamines. The tertiary alkanolamines as used herein refer to trialkyl alkanolamines, such as dimethylethanolamine, diethylethanolamine, triethanolamine, methyldiethanolamine, triisopropanolamine. The tertiary ethoxylated alkylamines as used herein refer to trialkyl amines in which at least one of the alkyl groups is a $C_{12}$-$C_{18}$ alkyl group and the remaining alkyl groups are hydroxyethyl groups. The Ethomeen™ products of Akzo Nobel, such as Ethomeen C/12, Ethomeen C/15, Ethomeen C/25, Ethomeen S/12, Ethomeen S/15, Ethomeen S/25, Ethomeen T/12, Ethomeen T/15, Ethomeen T/20, Ethomeen T/25 and Ethomeen T/30 are typical tertiary ethoxylated alkylamines. The tertiary propoxylated alkylamines as used herein refer to trialkyl amines in which at least one of the alkyl groups is a $C_{12}$-$C_{18}$ alkyl group and the remaining alkyl groups are hydroxypropyl groups. The Propomeen™ products of Akzo Nobel, such as Propomeen O/12 and Propomeen T/12, are typical tertiary propoxylated alkylamines. The tertiary alkyldiamines as used herein refer to tetraalkyl diamines in which at least one of the alkyl groups is a $C_{12}$-$C_{18}$ alkyl group. The Duomeen™ products of Akzo Nobel, such as Duomeen T™ are typical tertiary alkyldiamines. The tertiary ethoxylated alkyldiamines as used herein refer to tetraalkyl diamines in which at least one of the alkyl groups is a $C_{12}$-$C_{18}$ alkyl group and the remaining alkyl groups are hydroxyethyl groups. The Ethoduomeen™ products of Akzo Nobel, such as Ethoduomeen T/13, Ethoduomeen T/20 and Etoduomeen T/25 are typical tertiary ethoxylated alkyldiamines.

The solvent or co-solvent is an alcohol which is the same as the ester portion of the second carboxylic acid herbicide ester. Suitable alcohols may be a $C_4$-$C_8$ alkyl or alkoxy-substituted alkyl alcohols, such as butanol, 2-methylpropanol, 1-methyl heptanol, 2-ethylhexanol, 2-butoxyethanol, 2-butoxy-1-methylethanol, 2-methoxy-1-methylethanol or cyclohexanol.

The emulsifiers used in the present invention are optional and can be anionic, cationic or nonionic in character. Typical emulsifiers include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

The emulsifiable concentrates of the present invention are generally comprised of from about 0.01 to about 40 weight percent of the first carboxylic acid herbicide in the form of the amine salt, from about 0.01 to about 70 weight percent of the second carboxylic acid herbicide in the form of the ester, from about 1 to about 60 weight percent of the alcoholic solvent and from about 0 to about 20 weight percent of the emulsifiers. More preferably, these emulsifiable concentrates are generally comprised of from about 1 to about 20 weight percent of the first carboxylic acid herbicide in the form of the amine salt, from about 10 to about 60 weight percent of the second carboxylic acid herbicide in the form of the ester, from about 5 to about 50 weight percent of the alcoholic solvent and from about 2 to about 10 weight percent of the emulsifiers.

In addition to the compositions and uses set forth above, the present invention also embraces the composition and use of these emulsifiable concentrates in combination with one or more additional compatible ingredients. Other additional ingredients may include, for example, one or more other pesticides, dyes, and any other additional ingredients providing functional utility, such as, for example, stabilizers, fragrances, viscosity-modifying additives, suspension aids, dispersants, and freeze-point depressants.

The emulsifiable concentrates are generally prepared by contacting the first carboxylic acid herbicide in the acid form with the tertiary amine in the alcohol solvent and with the second carboxylic acid herbicide ester and optionally any emulsifiers with stirring until a homogeneous solution is obtained. More particularly, while the order of addition is not critical, the tertiary amine can be conveniently added with stirring to a suspension of the first carboxylic acid herbicide in the acid form in the alcohol solvent. Once a clear solution is obtained, the second carboxylic acid herbicide ester and emulsifiers can be added and the resulting mixture stirred until a single phase is obtained.

Examples 1-18 illustrate the present invention.

EXAMPLE 1

Ethoxylated tallowalkylamine (7.4 g, Ethomeen T/12, from Akzo Nobel) was added with stirring at 45±5° C. to a suspension of technical aminopyralid acid (4.0 g, from Dow AgroSciences) and ethylene glycol monobutyl ether solvent (62.3 g, Butyl Cellosolve, from The Dow Chemical Company). Stirring was continued until a clear solution was obtained. To the above mixture, technical triclopyr butoxyethyl ester (16.5 g, from Dow AgroSciences) and emulsifiers including amine salt of dodecylbenzene sulfonate (3.3 g, Bio-Soft N-411, from Stepan), EO-PO block copolymer (3.6 g, Toximul 8320, from Stepan), and ethoxylated castor oil (3.0 g, Toximul 8242, from Stepan) were added with stirring until a single phase was obtained.

EXAMPLE 2

Ethoxylated soyaalkylamine (610.8 g, Ethomeen S/12, purity 98%, from Akzo Nobel) was added with stirring at 45±5° C. to a suspension of technical aminopyralid acid (344.1, purity 93%, from Dow AgroSciences) and ethylene glycol monobutyl ether solvent (4698 g, Butyl Cellosolve, from The Dow Chemical Company). Stirring was continued until a clear solution was obtained. To the above mixture, technical triclopyr butoxyethyl ester (1848.7 g, purity 96.3%, from Dow AgroSciences) and emulsifiers including amine salt of dodecylbenzene sulfonate (266.7 g, Ninate 411, from Stepan), EO-PO block copolymer (293.3 g, Toximul 8320, from Stepan), and ethoxylated castor oil (240 g, Toximul 8242, from Stepan) were added with stirring until a single phase was obtained.

EXAMPLE 3

Ethoxylated cocoalkylamine (12.58 g, Ethomeen C/12, purity 98%, from Akzo Nobel) was added with stirring at 45±5° C. to a suspension of technical aminopyralid acid (8.39, purity 95.3%, from Dow AgroSciences) and ethylene glycol monobutyl ether solvent (49.0 g, Butyl Cellosolve, from The Dow Chemical Company). Stirring was continued until a clear solution was obtained. To the above mixture, technical triclopyr butoxyethyl ester (34.66 g, purity 96.3%, from Dow AgroSciences) and emulsifiers including EO-PO block copolymer (3.67 g, Toximul 8320, from Stepan) and ethoxylated castor oil (3.0 g, Toximul 8242, from Stepan) were added with stirring until a single phase was obtained.

EXAMPLE 4

Ethoxylated cocoalkylamine (12.58 g, Ethomeen C/12, purity 98%, from Akzo Nobel) was added with stirring at 45±5° C. to a suspension of technical aminopyralid acid (8.39 g, purity 95.3%, from Dow AgroSciences) and ethylene glycol monobutyl ether solvent (39.1 g, Butyl Cellosolve, from The Dow Chemical Company). Stirring was continued until a clear solution was obtained. To the above mixture, technical triclopyr butoxyethyl ester (46.22 g, purity 96.3%, from Dow AgroSciences) and emulsifiers including EO-PO block copolymer (3.67 g, Toximul 8320, from Stepan) and ethoxylated castor oil (3.0 g, Toximul 8242, from Stepan) were added with stirring until a single phase was obtained.

EXAMPLE 5

Ethoxylated soyaalkylamine (3.34 g, Ethomeen S/12, purity 98%, from Akzo Nobel) was added with stirring at 45±5° C. to a suspension of technical aminopyralid acid (1.88 g, purity 93%, from Dow AgroSciences) and ethylene glycol monobutyl ether solvent (31.99 g, Butyl Cellosolve, from The Dow Chemical Company). Stirring was continued until a clear solution was obtained. To the above mixture, technical triclopyr butoxyethyl ester (69.32 g, purity 96.3%, from Dow AgroSciences) and emulsifiers including amine salt of dodecylbenzene sulfonate (3.33 g, Bio-Soft N-411, from Stepan), EO-PO block copolymer (3.67 g, Toximul 8320, from Stepan), and ethoxylated castor oil (3.0 g, Toximul 8242, from Stepan) were added with stirring until a single phase was obtained.

EXAMPLE 6

Ethoxylated soyaalkylamine (6.68 g, Ethomeen S/12, purity 98%, from Akzo Nobel) was added with stirring at 45±5° C. to a suspension of technical aminopyralid acid (3.76 g, purity 93%, from Dow AgroSciences) and ethylene glycol monobutyl ether solvent (27.84 g, Butyl Cellosolve, from The Dow Chemical Company). Stirring was continued until a clear solution was obtained. To the above mixture, technical triclopyr butoxyethyl ester (69.32 g, purity 96.3%, from Dow AgroSciences) and emulsifiers including amine salt of dodecylbenzene sulfonate (3.33 g, Bio-Soft N-411, from Stepan), EO-PO block copolymer (3.67 g, Toximul 8320, from Stepan), and ethoxylated castor oil (3.0 g, Toximul 8242, from Stepan) were added with stirring until a single phase was obtained.

EXAMPLE 7

Ethoxylated cocoalkylamine (5.93 g, Ethomeen C/12, purity 98%, from Akzo Nobel) was added with stirring at 45±5° C. to a suspension of technical clopyralid acid (3.64 g, purity 92.2%, from Dow AgroSciences) and ethylene glycol monobutyl ether solvent (27.95 g, Butyl Cellosolve, from The Dow Chemical Company). Stirring was continued until a clear solution was obtained. To the above mixture, technical triclopyr butoxyethyl ester (69.32 g, purity 96.3%, from Dow AgroSciences) and emulsifiers including amine salt of dodecylbenzene sulfonate (3.33 g, Bio-Soft N-411, from Stepan), EO-PO block copolymer (3.67 g, Toximul 8320, from Stepan), and ethoxylated castor oil (3.0 g, Toximul 8242, from Stepan) were added with stirring until a single phase was obtained.

EXAMPLE 8

Ethoxylated cocoalkylamine (4.72 g, Ethomeen C/12, purity 98%, from Akzo Nobel) was added with stirring at 45±5° C. to a suspension of technical picloram acid (4.49 g, purity 77.9%, from Dow AgroSciences) and ethylene glycol monobutyl ether solvent (28.20 g, Butyl Cellosolve, from The Dow Chemical Company). Stirring was continued until a clear solution was obtained. To the above mixture, technical triclopyr butoxyethyl ester (69.32 g, purity 96.3%, from Dow AgroSciences) and emulsifiers including amine salt of dodecylbenzene sulfonate (3.33 g, Bio-Soft N-411, from Stepan), EO-PO block copolymer (3.67 g, Toximul 8320, from Stepan), and ethoxylated castor oil (3.0 g, Toximul 8242, from Stepan) were added with stirring until a single phase was obtained.

EXAMPLE 9

Ethoxylated oleylamine (6.70 g, Ethomeen O/12, purity 98%, from Akzo Nobel) was added with stirring at 45±5° C. to a suspension of technical aminopyralid acid (3.67 g, purity 95.3%, from Dow AgroSciences) and ethylene glycol monobutyl ether solvent (27.05 g, Butyl Cellosolve, from The Dow Chemical Company). Stirring was continued until a clear solution was obtained. To the above mixture, technical triclopyr butoxyethyl ester (69.32 g, purity 96.3%, from Dow AgroSciences) and emulsifiers including amine salt of dodecylbenzene sulfonate (3.33 g, Bio-Soft N-411, from Stepan), EO-PO block copolymer (3.67 g, Toximul 8320, from Stepan), and ethoxylated castor oil (3.0 g, Toximul 8242, from Stepan) were added with stirring until a single phase was obtained.

EXAMPLE 10

Ethoxylated soyaalkylamine (9.20 g, Ethomeen S/15, purity 98%, from Akzo Nobel) was added with stirring at 45±5° C. to a suspension of technical aminopyralid acid (3.67 g, purity 95.3%, from Dow AgroSciences) and ethylene glycol monobutyl ether solvent (27.84 g, Butyl Cellosolve, from The Dow Chemical Company). Stirring was continued until a clear solution was obtained. To the above mixture, technical triclopyr butoxyethyl ester (69.32 g, purity 96.3%, from Dow AgroSciences) and emulsifiers including amine salt of dodecylbenzene sulfonate (3.33 g, Bio-Soft N-411, from Stepan), EO-PO block copolymer (3.67 g, Toximul 8320, from Stepan), and ethoxylated castor oil (3.0 g, Toximul 8242, from Stepan) were added with stirring until a single phase was obtained.

EXAMPLE 11

Propoxylated oleylamine (7.23 g, Propomeen O/12, purity 98%, from Akzo Nobel) was added with stirring at 45±5° C. to a suspension of technical aminopyralid acid (3.67 g, purity 95.3%, from Dow AgroSciences) and ethylene glycol monobutyl ether solvent (26.51 g, Butyl Cellosolve, from The Dow Chemical Company). Stirring was continued until a clear solution was obtained. To the above mixture, technical triclopyr butoxyethyl ester (69.32 g, purity 96.3%, from Dow AgroSciences) and emulsifiers including amine salt of dodecylbenzene sulfonate (3.33 g, Bio-Soft N-411, from Stepan), EO-PO block copolymer (3.67 g, Toximul 8320, from Stepan), and ethoxylated castor oil (3.0 g, Toximul 8242, from Stepan) were added with stirring until a single phase was obtained.

EXAMPLE 12

Ethoxylated tallowediamine (4.37 g, Ethoduomeen T/13, from Akzo Nobel) was added with stirring at 45±5° C. to a suspension of technical aminopyralid acid (3.76 g, purity 93%, from Dow AgroSciences) and ethylene glycol monobutyl ether solvent (20.0 g, Butyl Cellosolve, from The Dow Chemical Company). Stirring was continued until a clear solution was obtained. To the above mixture, technical triclopyr butoxyethyl ester (69.32 g, purity 96.3%, from Dow AgroSciences), Aromatic 150 (12.2 g, from ExxonMobil), and emulsifiers including amine salt of dodecylbenzene sulfonate (3.3 g, Bio-Soft N-411, from Stepan), EO-PO block copolymer (3.60 g, Toximul 8320, from Stepan) and ethoxylated castor oil (3.0 g, Agnique CSO 40, from Cognis) were added with stirring until a single phase was obtained.

EXAMPLE 13

Trimethyl tallowediamine (3.7 g, Duomeen T™, from Akzo Nobel) was added with stirring at 45±5° C. to a suspension of technical aminopyralid acid (3.76 g, purity 93%, from Dow AgroSciences) and ethylene glycol monobutyl ether solvent (17.0 g, Butyl Cellosolve, from The Dow Chemical Company). Stirring was continued until a clear solution was obtained. To the above mixture, technical triclopyr butoxyethyl ester (69.32 g, purity 96.3%, from Dow AgroSciences), Aromatic 150 (16.9 g, from ExxonMobil), and emulsifiers including EO-PO block copolymer (3.60 g, Toximul 8320, from Stepan) and ethoxylated castor oil (3.0 g, Agnique CSO 40, from Cognis) were added with stirring until a single phase was obtained.

EXAMPLE 14

Tallowalkyl-dimethylamine (5.4 g, Armeen DMTD, from Akzo Nobel) was added with stiffing at 45±5° C. to a suspension of technical aminopyralid acid (3.76 g, purity 93%, from Dow AgroSciences) and ethylene glycol monobutyl ether solvent (17.0 g, Butyl Cellosolve, from The Dow Chemical Company). Stirring was continued until a clear solution was obtained. To above mixture, technical triclopyr butoxyethyl ester (69.3 g, purity 96.3%, from Dow AgroSciences), Aromatic 150 (15.2 g, from ExxonMobil), and emulsifiers including EO-PO block copolymer (3.60 g, Toximul 8320, from Stepan), and ethoxylated castor oil (3.0 g, Agnique CSO 40, from Cognis) were added with stirring until a single phase was obtained.

EXAMPLE 15

Ethoxylated tallowalkylamine (5.47 g, Ethomeen T/12, from Akzo Nobel) was added with stiffing at 45±5° C. to a suspension of technical aminopyralid acid (3.23 g, purity 93%, from Dow AgroSciences) and ethylene glycol monobutyl ether solvent (25 g, Butyl Cellosolve, from The Dow Chemical Company). Stirring was continued until a clear solution was obtained. To the above mixture, technical triclopyr butoxyethyl ester (26 g, purity 96.3%, from Dow AgroSciences), picloram isooctyl (9.25 g, purity 95%, from Dow AgroSciences), methylated vegetable oil (27.7 g, Edenor ME C12-18, from Cognis), and emulsifiers including amine salt of dodecylbenzene sulfonate (3.0 g, Bio-Soft N-411, from Stepan), EO-PO block copolymer (4.0 g, Toximul 8320, from Stepan), and ethoxylated castor oil (3.0 g, Toximul 8242, from Stepan) were added with stiffing until a single phase was obtained.

EXAMPLE 16

Ethoxylated tallowalkylamine (5.47 g, Ethomeen T/12, from Akzo Nobel) was added with stiffing at 45±5° C. to a suspension of technical aminopyralid acid (3.23 g, purity 93%, from Dow AgroSciences) and ethylene glycol monobutyl ether solvent (25 g, Butyl Cellosolve, from The Dow Chemical Company). Stirring was continued until a clear solution was obtained. To the above mixture, technical triclopyr butoxyethyl ester (26 g, purity 96.3%, from Dow AgroSciences), picloram isooctyl (9.25 g, purity 95%, from Dow AgroSciences), Aromatic solvent (28.1 g, Aromatic 150ND, from Exxon), and emulsifiers including amine salt of dodecylbenzene sulfonate (3.0 g, Bio-Soft N-411, from Stepan), EO-PO block copolymer (4.0 g, Toximul 8320, from Stepan), and ethoxylated castor oil (3.0 g, Toximul 8242, from Stepan) were added with stirring until a single phase was obtained.

EXAMPLE 17

Ethoxylated soyaalkylamine (8.68 g, Ethomeen S/12, from Akzo Nobel) was added with stirring at 45±5° C. to a suspension of technical aminopyralid acid (5.25 g, purity 95.3%, from Dow AgroSciences), 2-ethylhexanol (20.53 g, from Aldrich), and dimethylalkyl amide (30 g, Agnique KE 3658, from Cognis). Stirring was continued until a clear solution was obtained. To the above mixture, pre-melted technical fluoroxypyr meptyl technical (22.1 g, purity 97.7%, from Dow AgroSciences), picloram isooctyl (15.4 g, purity 95%, from Dow AgroSciences) and emulsifiers including amine salt of dodecylbenzene sulfonate (3.3 g, Bio-Soft N-411, from Stepan), EO-PO block copolymer (3.7 g, Toximul 8320, from Stepan), and ethoxylated castor oil (3.0 g, Toximul 8242, from Stepan) were added with stirring until a single phase was obtained.

EXAMPLE 18

The stability of the emulsifiable concentrates prepared in Examples 1-17 were assessed in accelerated storage tests after 2 weeks at 54° C. and after 8 weeks at 40° C. The results are summarized in Table 1. All examples demonstrate active ingredient stability of at least 95.0% after 2 weeks accelerated storage at 54° C. or 8 weeks accelerated storage at 40° C.

TABLE 1

Chemical Stability of Examples 1-17 During Storage at Accelerated Storage Temperature

| Example | % Retention of Active 1 | | % Retention of Active 2 | | % Retention of Active 3 | |
|---|---|---|---|---|---|---|
| | 2-wk at 54° C. | 8-wk at 40° C. | 2-wk at 54° C. | 8-wk at 40° C. | 2-wk at 54° C. | 8-wk at 40° C. |
| 1[a] | 96.7 | 96.2 | 99.9 | 99.9 | | |
| 2[a] | 99.9 | 99.5 | 99.5 | 98.1 | | |
| 3[a] | 97.9 | 96.6 | 98.0 | 96.7 | | |
| 4[a] | 99.7 | 95.1 | 96.4 | 95.2 | | |
| 5[a] | 96.7 | 98.0 | 98.6 | 97.6 | | |
| 6[a] | 99.9 | 99.5 | 99.5 | 98.1 | | |
| 7[a] | 99.3 | 97.7 | 99.1 | 95.7 | | |
| 8[a] | 98.7 | n/a | 98.8 | n/a | | |
| 9[a] | 96.0 | 95.3 | 95.9 | 95.1 | | |
| 10[a] | 96.2 | 95.8 | 95.7 | 95.1 | | |
| 11[a] | 96.7 | 96.7 | 95.9 | 95.1 | | |
| 15[b] | 97.9 | n/a | 95.0 | n/a | 97.0 | n/a |
| 16[b] | 99.9 | n/a | 95.5 | n/a | 97.8 | n/a |
| 17[c] | 99.9 | n/a | 99.9 | n/a | 99.9 | n/a |

[a]Active 1: aminopyralid; Active 2: triclopyr butotyl;
[b]Active 1: aminopyralid; Active 2: picloram isooctyl; Active 3: triclopyr butotyl;
[c]Active 1: aminopyralid; Active 2: picloram isooctyl; Active 3: fluroxypyr meptyl.

What is claimed:

1. A stable emulsifiable concentrate which comprises:
   a) from about 0.01 to about 40 weight percent of a first carboxylic acid herbicide selected from the group consisting of aminopyralid, picloram, clopyralid and triclopyr, wherein the first carboxylic acid herbicide is in the form of a tertiary amine salt in which the tertiary amine has the formula

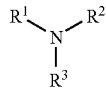

wherein $R^1$, $R^2$ and $R^3$ independently represent a $C_1$-$C_{18}$ alkyl, optionally substituted with hydroxyl, amino or alkoxy groups, in which at least one of $R^1$, $R^2$ and $R^3$ represents a $C_{12}$-$C_{18}$ alkyl group;
   b) from about 0.01 to about 70 weight percent of a second carboxylic acid herbicide selected from the group consisting of triclopyr, fluroxypyr and picloram, wherein the second carboxylic acid herbicide is in the form of a $C_4$-$C_8$ alkyl or alkoxy-substituted alkyl ester;
   c) from about 1 to about 60 weight percent of $C_4$-$C_8$ alkyl or alkoxy-substituted alkyl alcohol solvent or co-solvent which is the same as the alcohol which forms the ester portion of the second carboxylic acid herbicide in the form of a $C_4$-$C_8$ alkyl or alkoxy-substituted alkyl ester; and
   d) optionally, one or more emulsifiers present in an amount up to 20 weight percent.

2. The stable emulsifiable concentrate of claim 1 in which the tertiary amine salt is a tertiary alkylamine, a tertiary alkanolamine, a tertiary ethoxylated alkylamine, a tertiary propoxylated alkylamine, a tertiary alkyldiamine, a tertiary ethoxylated alkyldiamine, a tertiary propoxylated alkyldiamine and mixtures thereof.

3. The stable emulsifiable concentrate of claim 1 in which the second carboxylic acid herbicide in the form of a $C_4$-$C_8$ alkyl or alkoxy-substituted alkyl ester is a butotyl, meptyl, or isooctyl ester.

4. The stable emulsifiable concentrate of claim 1 which comprises from about 1 to about 20 weight percent of the first carboxylic acid herbicide in the form of the amine salt, from about 10 to about 60 weight percent of the second carboxylic acid herbicide in the form of the ester, from about 5 to about 50 weight percent of the alcoholic solvent and from about 2 to about 10 weight percent of the emulsifiers.

5. A method of preparing the emulsifiable concentrate of claim 1, which comprises contacting the first carboxylic acid herbicide in the acid form with the tertiary amine in the alcohol solvent and with the second carboxylic acid herbicide ester and optionally, any emulsifiers with stirring until a homogeneous solution is obtained.

* * * * *